(12) United States Patent
Bradaric-Baus et al.

(10) Patent No.: US 7,608,713 B2
(45) Date of Patent: Oct. 27, 2009

(54) TERTIARY PHOSPHINES AND THEIR METHODS OF PREPARATION

(75) Inventors: Christine J. Bradaric-Baus, Stony Creek (CA); Yuehui Zhou, Toronto (CA)

(73) Assignee: Cytec Canada Inc., Niagara Falls, Ontario (CA)

( * ) Notice: Subject to any disclaimer, the term of this patent is extended or adjusted under 35 U.S.C. 154(b) by 244 days.

(21) Appl. No.: 10/548,777

(22) PCT Filed: Mar. 8, 2004

(86) PCT No.: PCT/US2004/007031

§ 371 (c)(1),
(2), (4) Date: Aug. 14, 2006

(87) PCT Pub. No.: WO2004/094440

PCT Pub. Date: Nov. 4, 2004

(65) Prior Publication Data

US 2007/0037981 A1    Feb. 15, 2007

(30) Foreign Application Priority Data

Mar. 31, 2003   (CA) .................................... 2424225

(51) Int. Cl.
*C07F 9/06*   (2006.01)
(52) U.S. Cl. .............................. 546/22; 548/413; 568/12
(58) Field of Classification Search ................... 546/22; 548/413; 568/12
See application file for complete search history.

(56) References Cited

FOREIGN PATENT DOCUMENTS

EP   0184872   *   6/1986

OTHER PUBLICATIONS

Zabotina et al., Synthesis of 4,4-dimethyl-3,5-bis(diphenylphosphino)cyclohexanone, Tetrahedron, 57 (2001) 10177-10180.*
Couret et al., Addition of germyl- and silylphosphines to a-ethylenic aldehydes and ketones, Journal of Organometallic Chemistry (1975), 91(1), 11-30.*
Van Doorn et al., Addition of diphenylphosphine to maleic anhydride and related compounds, Phosphorus, Sulfur and Silicon and the Related Elements (1990), 47(3-4), 253-60.*
Issleib et al., Alkali-phosphorus compounds and their reactive behavior. LXXI. Synthesis and reaction behavior of (3-oxoalkyl)-organophosphines, Phosphorus and the Related Group V Elements (1973), 3(4), 141-52, Abstract.*

* cited by examiner

*Primary Examiner*—Yvonne Eyler
*Assistant Examiner*—Chukwuma O Nwaonicha
(74) *Attorney, Agent, or Firm*—Fran S. Wasserman

(57) ABSTRACT

Tertiary phosphines are prepared by reacting a phosphine ($PH_3$ or a primary or secondary phosphine) with a cyclic alpha,beta-unsaturated carbonyl compound having no more than one C=C double bond conjugated with a carbonyl group. The inventive tertiary phosphines can have R groups that are the same or different. The inventive tertiary phosphines may be used as ligands for metal catalysts or as starting materials for preparing phosphonium salts or ylids.

29 Claims, 3 Drawing Sheets

TERTIARY PHOSPHINES AND THEIR METHODS OF PREPARATION

CROSS-REFERENCE TO RELATED APPLICATIONS

This application is a U.S. National Phase application filed under 35 U.S.C. §371 of International Application No. PCT/US2004/007031 filed Mar. 8, 2004.

FIELD OF THE INVENTION

The present invention relates to the field of organic chemistry. In particular, the present invention relates to tertiary phosphines and their methods of preparation.

BACKGROUND

Tertiary phosphines find utility in several areas of organic chemistry, for example as starting materials for making phosphonium salts and ylids and as ligands in metal-carbene catalysts.

Some bulky tertiary phosphines, such as tricyclohexylphosphine, have been reported to be useful as catalyst ligands. For example, bulky tertiary phosphines find utility as ligands for metal catalysts, such as the ruthenium-based Grubbs catalyst (named after its inventor, Robert H. Grubbs). Notably, metal-carbene catalysts having tertiary phosphine ligands can be used as catalysts in several types of reactions, including: olefin metathesis reactions (for a recent review, see Rouhi, A. M. (2002) *Chemical and Engineering News*. pp. 29-33; see also: Grubbs et al. (1995) *Acc. Chem. Res.*, vol. 28, p. 446-452; Grubbs et al. (1998) *Tetrahedron*, vol. 54, pp. 4413-4450; Chatterjee et al. (1999) *Org. Lett.* Vol. 1, pp. 1751-1753); palladium-catalysed Suzuki cross couplings (Nethrton et al. (2001) *J. Am. Chem. Soc.*, vol. 123, pp. 10099-10100; Littke et al. (2000) *J. Am. Chem. Soc.*, vol. 122, pp. 4020-4028); and palladium-catalysed Heck reactions (A. F. Littke and G. C. Fu, (1999) *J. Org. Chem.*, vol. 64, pp. 10-11; Cabri et al. (1995) *Acc. Chem. Res.*, vol. 28, pp. 2-7).

A variety of tertiary phosphines can be prepared by reacting phosphorus trichloride with a Grignard reagent or with an organolithium compound, followed by aqueous workup, extraction and distillation. However, these processes have several disadvantages, in that materials used in these processes are expensive, corrosive, difficult to prepare owing to their sensitivity to moisture, and cumbersome to handle on a large scale. In addition, these processes generate large amount of waste. Further, these processes usually proceed quickly to the tertiary phosphine and are ideal for preparing a tertiary phosphine having identical radicals but are less suitable for preparing a tertiary phosphine having a particular composition of non-identical radicals.

Alternatively, phosphine gas ($PH_3$) can be reacted with an alkene under free radical conditions to produce primary, secondary and tertiary phosphines. This process advantageously avoids the use of organometallic compounds. However, this process may be less suitable for producing certain tertiary phosphines, such as tertiary phosphines that have several sterically bulky radicals attached to the central phosphorus atom. For example, addition of cyclohexene to $PH_3$ under free radical conditions favours the production of dicyclohexylphosphine and provides poor yields of tricyclohexylphosphine.

There have been some reports in the literature describing the preparation of cyclic and bicyclic tertiary phosphines (i.e. where the phosphorus atom is a ring member in a cyclic or bicyclic structure, respectively) via double Michael-additions of primary phosphines to conjugated dienones (Y. Kashman and Benady, E. (1972) *Tetrahedron*, vol. 28, pp. 4091-4098; E. Y. Zabotina et al. (2001) *Tetrahedron*, vol. 57, pp. 10177-10180; and WO 02/064249). However, this approach is limited to the preparation of cyclic and bicyclic phosphines.

SUMMARY OF THE INVENTION

In one aspect, the present invention provides a compound of formula I:

wherein:
$R^X$ is $R^1$ or $R^3$,
$R^Y$ is $R^2$ or $R^3$, and
$R^Z$ is $R^3$;

and wherein:
each of $R^1$ and $R^2$ is independently hydrocarbyl, and $R^3$ is

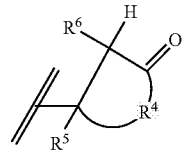

wherein:
$R^4$ and the $CR^5$—$CHR^6$—CO group to which $R^4$ is bonded form:
(i) a substituted or unsubstituted five- to eight-membered ring optionally containing one, two, or three heteroatoms selected from the group consisting of N, O and S;
(ii) a substituted or unsubstituted fused bicycle having two or three fused five- or six-membered rings optionally containing one, two, or three heteroatoms selected from the group consisting of N, O and S; or
(iii) a substituted or unsubstituted seven- to eight-membered bridged bicycle optionally containing one, two, or three heteroatoms selected from the group consisting of N, O and S;
$R^5$ is hydrogen or an unsubstituted, unbranched $C_1$-$C_4$ hydrocarbyl; and
$R^6$ is hydrogen or an unsubstituted $C_1$-$C_4$ hydrocarbyl;
with the proviso that $R^3$ cannot have a C=C double bond conjugated with a carbonyl group.

In another aspect, the present invention provides a method of making a compound of formula I, the method comprising contacting a compound of formula II:

wherein each of $R^7$ and $R^8$ is independently a hydrogen or a hydrocarbyl, with a compound of formula III:

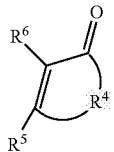

wherein $R^4$ and the $CR^5\!\!=\!\!CR^6\!\!-\!\!CO$ group to which $R^4$ is bonded form:

(i) a substituted or unsubstituted five- to eight-membered ring optionally containing one, two, or three heteroatoms selected from the group consisting of N, O and S;

(ii) a substituted or unsubstituted fused bicycle having two or three fused five- or six-membered rings optionally containing one, two, or three heteroatoms selected from the group consisting of N, O and S; or (iii) a substituted or unsubstituted seven- to eight-membered bridged bicycle optionally containing one, two, or three heteroatoms selected from the group consisting of N, O and S;

and $R^5$ and $R^6$ are defined as above;

with the proviso that the compound of formula III has no more than one C=C double bond conjugated with a carbonyl group.

In another aspect, the present invention provides use of a compound of formula I as a ligand for a metal catalyst, such as a ruthenium catalyst or a palladium catalyst.

DETAILED DESCRIPTION

Compounds of Formula I

Figure 1:
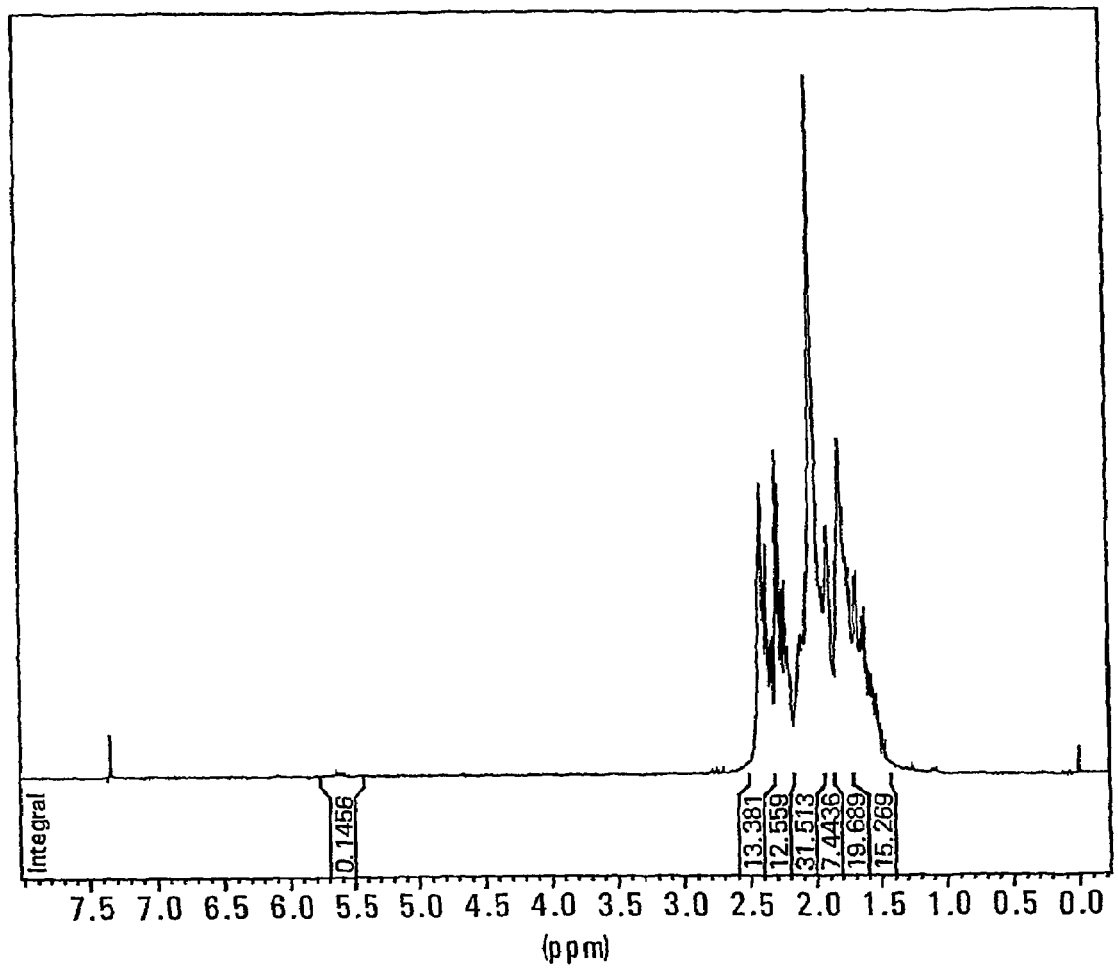
FIG. 1 is a $^1$H NMR (nuclear magnetic resonance) spectrum of 3-(9-phosphabicyclo[3.3.1]nonan-9-yl)-cyclohexan-1-one.

Suitable hydrocarbyl groups for $R^1$, $R^2$, $R^7$, and $R^8$, include: unsubstituted or substituted $C_1$-$C_{30}$ alkyl; unsubstituted or substituted $C_3$-$C_8$ cycloalkyl; unsubstituted or substituted $C_2$-$C_{30}$ alkenyl; unsubstituted or substituted $C_2$-$C_{30}$ alkynyl; unsubstituted or substituted $C_6$-$C_{18}$ aryl; unsubstituted or substituted $C_7$-$C_{30}$ aralkyl; unsubstituted or substituted $C_2$-$C_{30}$ heteroalkyl containing one or two heteroatoms selected from the group consisting of N, O or S; unsubstituted or substituted $C_3$-$C_8$ heterocycle containing one or two heteroatoms selected from the group consisting of N, O or S; unsubstituted or substituted $C_3$-$C_{30}$ heteroalkenyl containing one or two heteroatoms selected from the group consisting of N, O or S; unsubstituted or substituted $C_3$-$C_{30}$ heteroalkynyl containing one or two heteroatoms selected from the group consisting of N, O or S; unsubstituted or substituted $C_6$-$C_{18}$ heteroaryl containing one or two heteroatoms selected from the group consisting of N, O or S; unsubstituted or substituted $C_7$-$C_{30}$ heteroaralkyl containing one or two heteroatoms selected from the group consisting of N, O or S. For the most part, it is contemplated that hydrocarbyl groups shall have not more than 20 carbon atoms.

$R^1$ and $R^2$ and the phosphorus atom to which $R^1$ and $R^2$ are bonded can form a six- to eight-membered heterocycle, a seven- to ten-membered heterobicycle, or a ten-membered heterotricycle. Similarly, when both $R^7$ and $R^8$ are hydrocarbyl, $R^7$ and $R^8$ and the phosphorus atom to which $R^7$ and $R^8$ are bonded can form a six- to eight-membered heterocycle, a seven- to ten-membered heterobicycle, or a ten-membered heterotricycle.

It is possible for the groups $R^1$, $R^2$, $R^7$, and $R^8$, to bear substituents, or to include heteroatoms, provided that the substituents or heteroatoms do not interfere with the preparation of the compounds of the invention, and do not adversely affect the desired properties of the tertiary phosphine. Acceptable substituents may include hydroxyl, halo, alkoxy, alkylthio, carboxy, and acetyl groups, and heteroatoms that may be acceptable include nitrogen, oxygen and sulphur. If necessary, one of skill in the art can readily determine whether substituents or heteroatoms of the hydrocarbyl groups interfere with preparation or desired properties of the compounds by routine experimentation that does not involve the exercise of any inventive faculty.

In many cases, $R^1$, $R^2$, $R^7$, and $R^8$ will be unsubstituted $C_1$-$C_{18}$ alkyl, unsubstituted $C_3$-$C_8$ cycloalkyl, or unsubstituted $C_6$-$C_{10}$ aryl. Thus, specific examples of values for $R^1$, $R^2$, $R^7$, and $R^8$, include: methyl, ethyl, n-propyl, isopropyl, n-butyl, iso-butyl, tert-butyl, n-pentyl, iso-pentyl, cyclopentyl, n-hexyl, cyclohexyl, phenyl, norbornyl, (2,4,4'-trimethyl)pentyl, cyclooctyl, tetradecyl, etc.

Examples of heterobicycles that can be formed when the phosphorus atom is bonded to $R^7$ and $R^8$ include: 9-phosphabicyclo[3.3.1]nonane, 9-phosphabicyclo[4.2.1]nonane, 9-phosphabicyclo[3.3.1]nonan-3-one, 4,8-dimethyl-2-phosphabicyclo[3.1.1]nonane, and 2,5-di($C_1$-$C_4$ alkyl)-7-phosphabicyclo[2.2.1]heptane. Examples of heterotricycles that can be formed when the phosphorus atom is bonded to $R^7$ and $R^8$ include: 1,3,5,7-tetra($C_1$-$C_4$ alkyl)-2,4,8-trioxa-6-phosphaadamantane.

Examples of heterobicycles that can be formed when the phosphorus atom is bonded to $R^1$ and $R^2$ include: 9-phosphabicyclo[3.3.1]non-9-yl, 9-phosphabicyclo[4.2.1]non-9-yl, 9-phosphabicyclo[3.3.1]nonan-3-on-9-yl, 4,8-dimethyl-2-phosphabicyclo[3.1.1]non-9-yl, and 2,5-di($C_1$-$C_4$ alkyl)-7-phosphabicyclo[2.2.1]hept-7-yl. Examples of heterotricycles that can be formed when the phosphorus atom is bonded to $R^2$ and $R^2$ include: 1,3,5,7-tetra($C_1$-$C_4$ alkyl)-2,4,8-trioxa-6-phosphaadamant-6-yl.

$R^4$ can bear substituents or include heteroatoms, provided that the substituents or heteroatoms do not interfere with the preparation or use of the compound. Acceptable substituents may include halo, and hydroxy, as well as hydrocarbyl groups such as alkyl, alkenyl and cycloalkyl groups, heteroatoms that may be acceptable include N, O and S. Mention is made of $C_1$-$C_8$ alkyl and alkenyl groups, straight chained or branched, $C_3$-$C_8$ cycloalkyl groups, and aryl groups such as phenyl or napthyl, aralkyl groups such as benzyl or phenethyl and alkaryl groups such as tolyl or xylyl. Other substituents include acyl, acyloxy, alkoxy, alkenoxy and aryloxy groups, again having up to about 8 carbon atoms. Substituents that are electron-withdrawing, for instance fluoro, hydroxy, trifluoromethyl, cyano, alkylcarbonyl and alkoxycarbonyl, may favour the reaction for preparing compounds of formula I. To avoid steric interference, $R^4$ can be chosen so that bulky substituents are not present on the carbon atom that is immediately adjacent to the $R^5$-bearing carbon atom (i.e. the carbon atom that bonds to the phosphorus atom). R⁴ can be unsaturated, provided that R⁴ is chosen so that the compound of formula III has no more than one C═C double bond conjugated with a carbonyl group and further that R³ does not have a C═C double bond conjugated with a carbonyl group.

Thus, suitable values for R⁴ include but are not limited to ethylene (—CH₂—CH₂—), propylene (—CH₂—CH₂—CH₂—), and (—CH₂—CH₂—CH₂—CH₂—CH₂—), and suitable values for R³ when it is a five- to eight-membered ring include 3-oxo-cyclopentyl, 3-oxo-cyclohexyl, and 3-oxo-cyclooctyl.

Examples of compounds of formula III when it is a five- to eight-membered ring include 2-cyclopenten-1-one, 2-cyclohexen-1-one, 2-cycloocten-1-one, isophorone (i.e. 3,5,5-trimethyl-2-cyclohexen-1-one), carvonone (i.e. 2-methyl-5-(1-methylethenyl)-2-cyclohexen-1-one), and dihydrocarvanone (i.e. 2-methyl-5-(1-methylethyl)-2-cyclohexen-1-one).

In the present context, two rings are said to be "fused" if they have one bond common to both rings. Thus, suitable values for R³ when it is a fused bicycle having two or three fused five- or six-membered rings include:

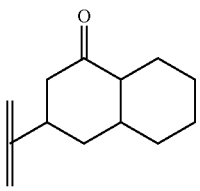 and 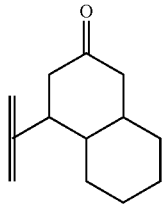

Examples of compounds of formula III when it is a fused bicycle having two or three fused five- or six-membered rings include:

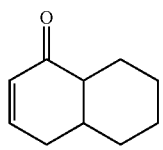 and 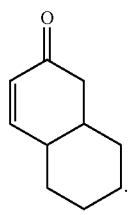

In the present context, a "bridged" bicyclic compound is a compound in which a bridge of atom(s) extends from one side of a ring to the other. Thus, suitable values for R³ when it is a seven- to eight-membered bridged bicycle include:

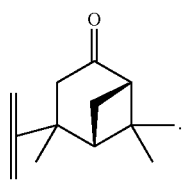

Examples of compounds of formula III when it is a seven- to eight-membered bridged bicycle include verbenone:

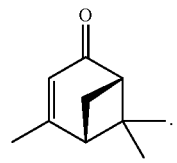

Suitable hydrocarbyl groups for R⁵ include: methyl, ethyl, n-propyl, and n-butyl. However, R⁵ is preferably hydrogen or methyl, and more preferably R⁵ is hydrogen.

Suitable hydrocarbyl groups for R⁶ include: methyl, ethyl, n-propyl, iso-propyl, n-butyl, iso-butyl and tert-butyl. However, when R⁶ is bulky, it may interfere with the rate of reaction of a compound of formula III with a phosphine of formula II. Therefore, in many cases it is preferred that R⁶ is hydrogen or methyl, and more preferred that R⁶ is hydrogen.

There is no critical upper limit to the number of carbon atoms that may be present in the compounds of formula I. However, for the most part it is contemplated that compounds of formula I shall contain no more than about 30 carbon atoms.

Tertiary phosphine compounds of formula I that may find utility, for example, as catalyst ligands and as starting materials for making phosphonium salts and ylids. It is noted that the R groups in tertiary phosphines of formula I can be the same or different, i.e. the tertiary phosphine can have identical or mixed radicals. The properties of the tertiary phosphine can be modified by varying the values and mixture of the R groups present on the phosphorus atom.

Tertiary phosphines having sterically bulky R groups are preferred in some applications. For example, bulky electron-rich tertiary phosphines may be preferred as catalyst ligands, e.g. for metal catalysts of reactions including but not limited to olefin metathesis, palladium-catalyzed Suzuki cross-coupling, palladium-catalyzed Heck reactions, hydroformylations, and carbonylations. For this reason, it may be preferred that R¹ and R² are cyclic, branched, or aromatic, or together with the phosphorus atom to which they are bonded form heterocycles, heterobicycles or heterotricycles. Branching can occur at the alpha or omega carbon or at any intermediate point. Sterically bulky R groups include branched $C_4$-$C_{18}$ alkyl, $C_3$-$C_8$ cycloalkyl, and $C_6$-$C_{10}$ aryl, any of which may be substituted or unsubstituted, but for the most part will be unsubstituted. Thus, specific examples of sterically bulky R groups include: iso-butyl, tert-butyl, n-pentyl, iso-pentyl, cyclopentyl, cyclohexyl, phenyl, norbornyl, cyclooctyl, (2,4,4'-trimethyl)pentyl, etc. Sterically bulky heterobicycles include: 9-phosphobicyclo[3.3.1]non-9-yl, 9-phosphabicyclo[4.2.1)]non-9-yl, 9-phosphabicyclo[3.3.1]nonan-3-on-9-yl, 4,8-dimethyl-2-phosphabicyclo[3.1.1]non-9-yl, and 2,5-di($C_1$-$C_4$ alkyl)-7-phosphabicyclo[2.2.1]hept-7-yl. Sterically bulky heterotricycles that can be formed when the phosphorus atom is bonded to R¹ and R² include: 1,3,5,7-tetra($C_1$-$C_4$ alkyl)-2,4,8-trioxa-6-phosphaadamant-6-yl.

Method for Preparing Compounds of Formula I

Tertiary phosphines of formula I can be prepared by reacting a phosphine of formula II (PH₃ or a primary or secondary phosphine, hereinafter referred to as a "starting phosphine") with an alpha,beta-unsaturated carbonyl compound of formula III having no more than one C═C double bond conjugated with a carbonyl group. By "conjugated" double bonds, we mean two double bonds separated by a single bond i.e.

C=C—C=C, C=C—C=O, etc. Compounds with a C=C double bond conjugted with a C=O group are known in the art as alpha, beta-unsaturated carbonyl compounds.

In general, the reaction proceeds over a wide range of temperatures, say between about 40° C. to about 180° C., often in the range of 50° C. to 70° C., and is often complete in 8 hours or less at these temperatures. Although the temperature of the reaction is not critical, lower temperatures will result in longer reaction times. When the reaction is carried out in the liquid phase at ambient pressure, there may be a practical upper limit to the reaction temperature that can be used, based on the carbonyl compound and starting phosphine reagents. The initial step of mixing the alpha,beta-unsaturated carbonyl compound and the starting phosphine reagents may be conveniently carried out at room temperature or slightly elevated temperature.

When the starting phosphine of formula II is liquid at the temperature to be used for carrying out the reaction, the pressure of the reaction is not critical, and the reaction may be conveniently carried out at atmospheric pressure, preferably under an inert atmosphere, such as nitrogen. However, when the starting phosphine is a gas at the temperature to be used for carrying out the reaction, the reaction is suitably carried out under pressure (e.g. in an autoclave) under an inert atmosphere, such as nitrogen. For example, $PH_3$ is a gas with boiling point of about −87° C. and some primary and secondary phosphines with small R groups (such as methylphosphine which has a boiling point of. −20°, ethylphosphine, dimethylphosphine, and diethylphosphine) have low boiling points and may be gaseous at the temperature to be used for carrying out the reaction.

The reaction can be carried out in the absence of solvent, in order to avoid a further step of purifying product away from solvent. However, the reaction can also be carried out in the presence of a solvent. In some cases, the presence of a solvent may be useful for controlling the temperature of the reaction, which is exothermic. Examples of suitable solvents include: toluene, ethanol, isopropanol, butanol, dimethylformamide, tributylphosphate, tritylphosphine oxide.

Unreacted starting materials may be removed, for example, by evaporation under vacuum.

The properties of the reagents may affect the overall course of the reaction. For example, the increased steric bulk of $R^3$ when it bears substituents may decrease the rate of reaction. This effect may be counteracted somewhat if the substituents have electron-withdrawing properties. Increased steric bulk around the phosphorus atom may decrease the overall rate of reaction. The presence of electron-withdrawing groups on the starting phosphine of formula II may also decrease the overall rate of reaction.

In many cases, the reaction proceeds readily without further addition of a promoter (i.e. an acid promoter or a base promoter). However, in some cases, for example where the alpha, beta-unsaturated carbonyl compounds of formula III or the phosphine is sterically hindered, adding an acid promoter or base promoter may enhance the rate of the reaction.

In one embodiment, the method of the current invention can be used to prepare tertiary phosphines that have bulky radicals, identical or mixed (i.e. non-identical). Tertiary phosphines having bulky radicals may find utility as catalyst ligands, e.g. for metal-carbene catalysts. Notably, tertiary phosphines having mixed radicals provide possibilities for catalyst ligands that have not yet been explored, due to the relative inaccessibility of tertiary phosphine ligands having mixed radicals.

The tertiary phosphines described herein may also find utility as starting materials, for example for making phosphonium salts or ylids.

The invention is further illustrated in the following non-limiting examples.

EXAMPLE 1

Preparation of 3-(di(iso-butyl)phosphino)cyclohexan-1-one

A 250 ml round-bottomed flask fitted with a condenser, nitrogen purge, and addition funnel was charged with 29.9 g (0.3 mol) 2-cyclohexen-1-one and heated to 45° C. with stirring. Di-(iso-butyl)phosphine (28.8 g, 0.2 mol) was gradually added to the flask via the addition funnel, over a period of 0.5 hour. When addition was complete, the temperature of the contents of the flask was slowly raised to 70° C. and maintained at that temperature for 3 hours, then cooled. Unreacted starting materials were removed by evaporation under reduced pressure at 120° C.

The product of the reaction was analyzed by $^1H$, $^{13}C$, and $^{31}P$ NMR (nuclear magnetic resonance spectroscopy) and GC/MS (Gas chromatography mass spectrometry).

Di-(iso-butyl)phosphinocyclohexan-1-one was obtained in 70.9% yield (55.1 g).

EXAMPLE 2

Preparation of 3-(dicyclohexylphosphino)cyclohexan-1-one

A 250 ml round-bottomed flask fitted with a condenser, nitrogen purge, and addition funnel was charged with a solution of 89.7 g (0.45 mol) dicyclohexylphosphine and heated to 60° C. with stirring. To the flask was added 50.8 g (0.53 mol) 2-cyclohexen-1-one over a period of 0.5 hour. When addition was complete, the temperature of the contents of the flask was slowly raised to 90° C. and maintained at that temperature for 6 hours, then cooled. Unreacted starting materials were removed by evaporation under reduced pressure at 150° C.

The product of the reaction was analyzed by $^1H$, $^{13}C$, and $^{31}P$ and GC/MS.

Dicyclohexylphosphinocyclohexan-1-one was obtained in 98.3% yield (140.5 g) and solidified to form a fine white powder.

EXAMPLE 3

Preparation of 3-(9-phosphabicyclo[3.3.1]nonan-9-yl)-cyclohexan-1-one 2-cyclohexenone (19.2 g, Aldrich, 95%, Mt. 96.13, 0.1897 mole) was added dropwise to a flask containing 9-phosphacyclo[3.3.1]nonane (72.8 g, 37%, Mt. 142, 0.1897 mole) and toluene under nitrogen flow and at 120° C., with stirring. The temperature of the reaction mixture was gradually increased to 160° C., accompanied by stripping off the toluene through the additional funnel. The reaction mixture was further refluxed at 160° C. for 9 hours. GC/MS showed that the 2-cyclohexenone was almost consumed. The crude product was dried on rotary-evaporator at 170° C. and 5 mmHg for 2 hours. The dried product was solid at room temperature and weighted 45 g (yield 99%).

Figure 2:
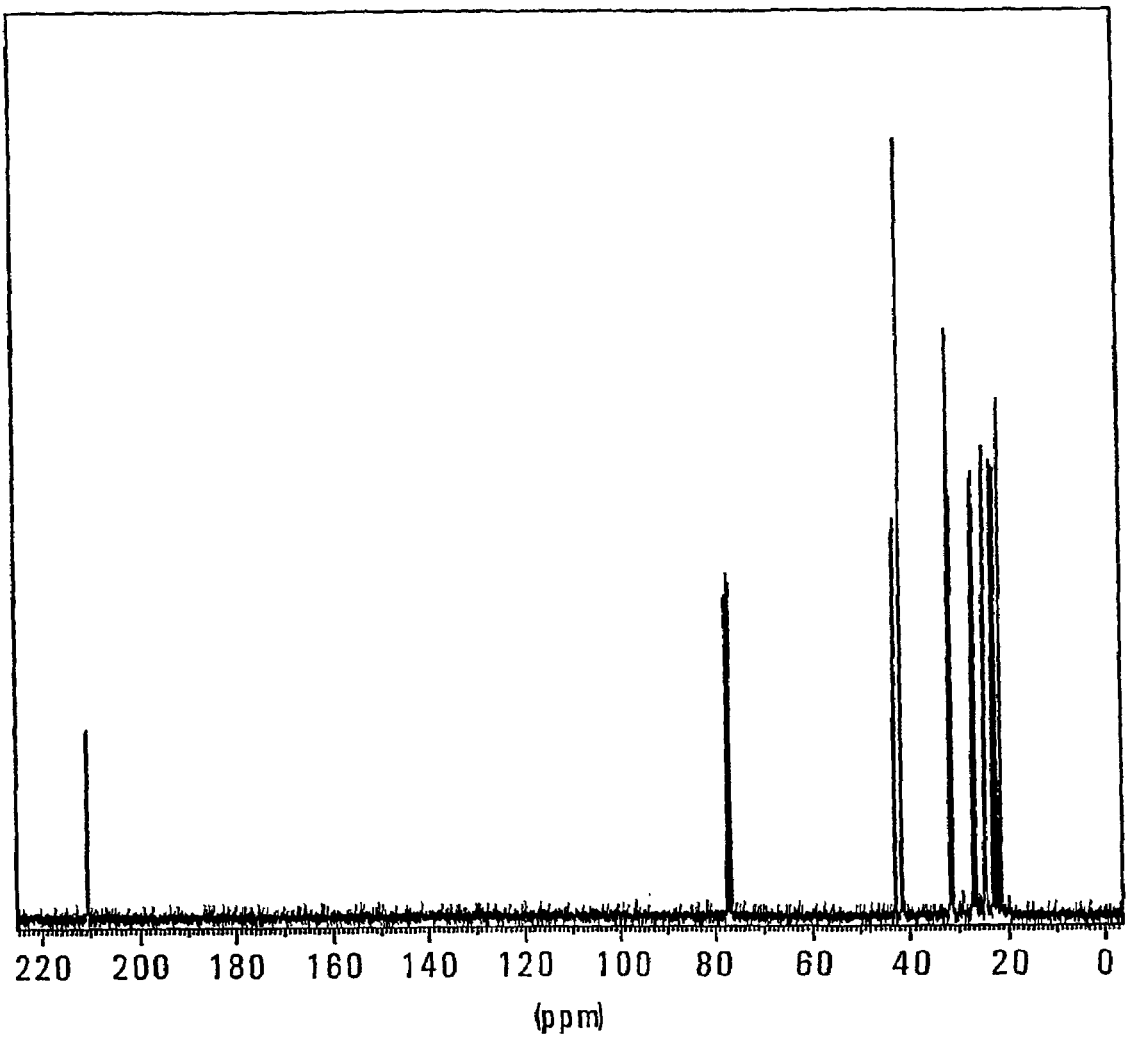
FIG. 2 is a $^{13}$C NMR spectrum of 3-(9-phosphabicyclo[3.3.1]nonan-9-yl)-cyclohexan-1-one.
Figure 3:
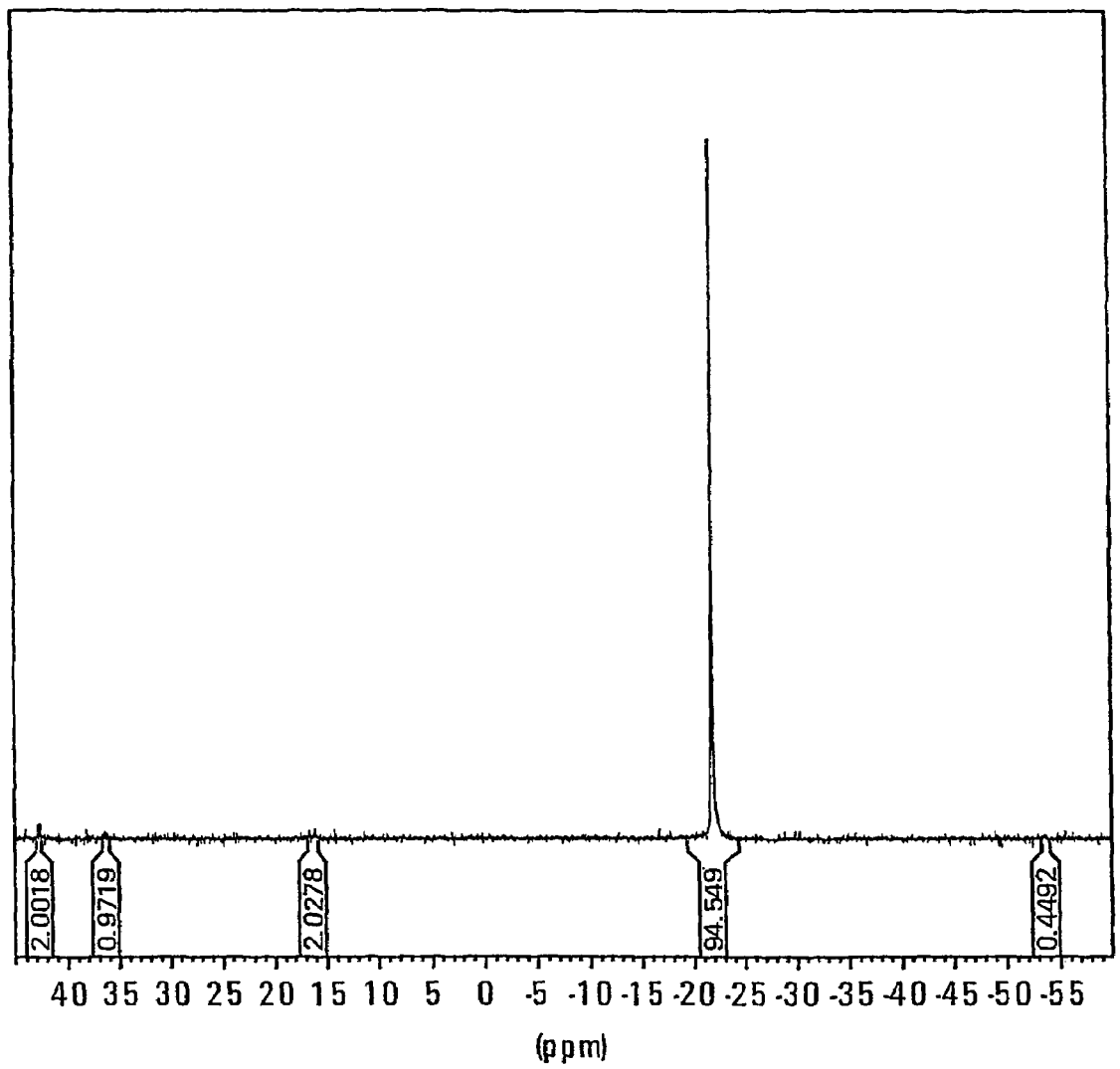
FIG. 3 is a $^{31}$P NMR spectrum of 3-(9-phosphabicyclo[3.3.1]nonan-9-yl)-cyclohexan-1-one.

The product of the reaction was analyzed by $^1H$, $^{13}C$, and $^{31}P$ (see FIGS. 1 to 3), confirming that the major product was 3-(9-phosphabicyclo[3.3.1]nonan-9-yl)-cyclohexan-1-one.

EXAMPLE 4

Preparation of di(cyclohexanon-3-yl)-cyclohexylphosphine

Cyclohexylphosphine (17.0 g, 98%, Mt. 116, 0.1436 mole) was added gradually (i.e. over a 30-hour period) through an additional funnel to a flask containing cyclohexenone (27.9 g, 95%, M.t. 96.13, 0.2757 mole) preheated (150° C.) solution in toluene (33 g), under nitrogen.

The reaction was followed by GC-MS analysis. Upon completion of addition of the cyclohexylphosphine, GC/MS showed peaks for compounds with molecular weights 212 and 308, corresponding respectively to the molecular weights of cyclohexylphosphinocyclhexan-1-one (the mono-substituted product) and di(cyclohexanon-3-yl)-cyclohexylphosphine (the di-substituted product). The mixture was refluxed for a further 8 hours. GC/MS analysis showed that the reaction mixture contained about 60% of the di(cyclohexanon-2-yl)-cyclohexylphosphine product.

What is claimed is:

1. A compound of formula I:
wherein:

$$\begin{array}{c} R^x \\ | \\ P\text{---}R^y \\ | \\ R^z \end{array} \quad (I)$$

$R^X$ is $R^1$ or $R^3$,
$R^Y$ is $R^2$ or $R^3$, and
$R^Z$ is $R^3$;
and wherein:
(A) $R^1$ and $R^2$ have the following values:
 (i) $R^1$ and $R^2$ and the phosphorus atom to which $R^1$ and $R^2$ are bonded form a seven-to ten-membered heterobicycle; or
 (ii) each of $R^1$ and $R^2$ is independently: unsubstituted $C_1$-$C_{30}$ alkyl; substituted $C_1$-$C_{30}$ alkyl; unsubstituted $C_3$-$C_8$ cycloalkyl; substituted $C_3$-$C_8$ cycloalkyl; unsubstituted $C_2$-$C_{30}$ alkenyl; substituted $C_2$-$C_{30}$ alkenyl; unsubstituted $C_2$-$C_{30}$ alkynyl; substituted $C_2$-$C_{30}$ alkynyl; unsubstituted $C_6$-$C_{18}$ aryl; substituted $C_6$-$C_{18}$ aryl; unsubstituted $C_7$-$C_{30}$ aralkyl; substituted $C_7$-$C_{30}$ aralkyl; unsubstituted $C_2$-$C_{30}$ heteroalkyl containing one or two heteroatoms which are N, O or S; substituted $C_2$-$C_{30}$ heteroalkyl containing one or two heteroatoms which are N, O or S; unsubstituted $C_3$-$C_8$ heterocycle containing one or two heteroatoms which are N, O or S; substituted $C_3$-$C_8$ heterocycle containing one or two heteroatoms which are N, O or S; unsubstituted $C_3$-$C_{30}$ heteroalkenyl containing one or two heteroatoms which are N, O or S; substituted $C_3$-$C_{30}$ heteroalkenyl containing one or two heteroatoms which are N, O or S; unsubstituted $C_3$-$C_{30}$ heteroalkynyl containing one or two heteroatoms which are N, O and S; substituted $C_3$-$C_{30}$ heteroalkynyl containing one or two heteroatoms which are N, O and S; unsubstituted $C_6$-$C_{18}$ heteroaryl containing one or two heteroatoms which are N, O or S; substituted $C_6$-$C_{18}$ heteroaryl containing one or two heteroatoms which are N, O or S; unsubstituted $C_7$-$C_{30}$ heteroaralkyl containing one or two heteroatoms which are N, O or S; and substituted $C_7$-$C_{30}$ heteroaralkyl containing one or two heteroatoms which are N, O or S; and (B) $R^3$ is selected from:

with the proviso that when $R^X$ and $R^Y$ are ethyl, $R^3$ cannot be 3-oxo-cyclopentyl.

2. The compound of claim 1, wherein $R^x$ is $R^1$ and $R^y$ is $R^2$.

3. The compound of claim 1, wherein:
 (i) $R^X$ is $R^1$ and is $R^3$; or
 (ii) $R^X$ is $R^3$ and $R^Y$ is $R^2$.

4. The compound of claim 1, wherein $R^X$ and $R^Y$ are both $R^3$.

5. The compound of claim 1, wherein each of $R^1$ and $R^2$ is independently selected from the group consisting of: unsubstituted $C_1$-$C_{18}$ alkyl, unsubstituted $C_3$-$C_8$ cycloalkyl, and unsubstituted $C_6$-$C_{10}$ aryl.

6. The compound of claim 5, wherein each of $R^1$ and $R^2$ is independently selected from the group consisting of: unsubstituted, branched $C_4$-$C_{18}$ alkyl, unsubstituted $C_3$-$C_8$ cycloalkyl, and unsubstituted $C_6$-$C_{10}$ aryl.

7. The compound of claim 6, wherein each of $R^1$ and $R^2$ is independently selected from the group consisting of: iso-butyl, tert-butyl, n-pentyl, iso-pentyl, cyclopentyl, cyclohexy, phenyl, norbonyl, cyclooctyl, and (2,4,4-trimethyl)pentyl.

8. The compound of claim 7, wherein $R^1$ and $R^2$ are both cyclohexyl.

9. The compound of claim 7, wherein $R^1$ and $R^2$ are both iso-butyl.

10. The compound of claim 1, wherein the heterobicycle is selected from the group consisting of:
 9-phosphabicyclo[3.3.1]non-9-yl,
 9-phosphabicyclo[4.2.1]non-9-yl,
 9-phosphabicyclo[3.3.1]nonon-3-on-9-yl,
 4,8-dimethyl-2-phosphabicyclo[3.1.1]non-9-yl, and
 2,5-di ($C_1$-$C_4$ alkyl)-7-phosphabicyclo[2.2.1]hept-7-yl.

11. A compound of formula I:

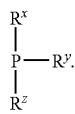

(I)

$R^X$ is $R^1$ or $R^3$,
$R^Y$ is $R^2$ or $R^3$, and
$R^Z$ is $R^3$,
and wherein:
(A) $R^1$ and $R^2$ have the following values:
(i) $R^1$ and $R^2$ and the phosphorus atom to which $R^1$ and $R^2$ are bonded form a seven-to ten-membered heterobicycle; or
(ii) each of $R^1$ and $R^2$ is independently: unsubstituted $C_1$-$C_{30}$ aklyl; substituted $C_1$-$C_{30}$ alkyl; unsubstituted $C_3$-$C_8$ cycloalkyl; substituted $C_3$-$C_8$ cycloalkyl; unsubstituted $C_2$-$C_{30}$ alkenyl; substituted $C_2$-$C_{30}$ alkenyl; unsubstituted $C_2$-$C_{30}$ alkynyl; substituted $C_2$-$C_{30}$ alkynyl; unsubstituted $C_6$-$C_{18}$ aryl; substituted $C_6$-$C_{18}$ aryl; unsubstituted $C_7$-$C_{30}$ aralkyl; substituted $C_7$-$C_{30}$ aralkyl; unsubstituted $C_2$-$C_{30}$ heteroalkyl containing one or two heteroatoms which are N, O or S; substituted $C_2$-$C_{30}$ heteroalkyl containing one or two heteroatoms which are N, O or S; unsubstituted $C_3$-$C_8$ heterocycle containing one or two heteroatoms which are N. O or S; substituted $C_3$-$C_8$ heterocycle containing one or two heteroatoms which are N, O or S; unsubstituted $C_3$-$C_{30}$ heteroalkenyl containing one or two heteroatoms which are N, O or S; substituted $C_3$-$C_{30}$ heteroalkenyl containing one or two heteroatoms which are N, O or S; unsubstituted $C_3$-$C_{30}$ heteroalkynyl containing one or two heteroatoms which are N, O and S; substituted $C_3$-$C_{30}$ heteroalkynyl containing one or two heteroatoms which are N, O and S; unsubstituted $C_6$-$C_{18}$ heteroaryl containing one or two heteroatoms which are N, O or S; substituted $C_6$-$C_{18}$ heteroaryl containing one or two heteroatoms which are N, O or S; unsubstituted $C_7$-$C_{30}$ heteroaralkyl containing one or two heteroatoms which are N, O or S; and substituted $C_7$-$C_{30}$ heteroaralkyl containing one or two heteroatoms which are N, O or S; and
(B) $R^3$ is:

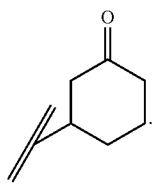

12. A compound of formula I:
wherein:

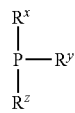

(I)

$R^X$ is $R^1$ or $R^3$,
$R^Y$ is $R^2$ or $R^3$, and
$R^Z$ is $R^3$,
and wherein:
(A) $R^1$ and $R^2$ have the following values:
(i) $R^1$ and $R^2$ and the phosphorus atom to which $R^1$ and $R^2$ are bonded form a seven-to ten-membered heterobicycle; or
(ii) each of $R^1$ and $R^2$ is independently: unsubstituted $C_1$-$C_{30}$ aklyl; substituted $C_1$-$C_{30}$ alkyl; unsubstituted $C_3$-$C_8$ cycloalkyl; substituted $C_3$-$C_8$ cycloalkyl; unsubstituted $C_2$-$C_{30}$ alkenyl; substituted $C_2$-$C_{30}$ alkenyl; unsubstituted $C_2$-$C_{30}$ alkynyl; substituted $C_{2.1}$-$C_{30}$ alkynyl; unsubstituted $C_6$-$C_{18}$ aryl; substituted $C_6$-$C_{18}$ aryl; unsubstituted $C_7$-$C_{30}$ aralkyl; substituted $C_7$-$C_{30}$ aralkyl; unsubstituted $C_2$-$C_{30}$ heteroalkyl containing one or two heteroatoms which are N, O or S; substituted $C_2$-$C_{30}$ heteroalkyl containing one or two heteroatoms which are N, O or S; unsubstituted $C_3$-$C_8$ heterocycle containing one or two heteroatoms which are N. O or S; substituted $C_3$-$C_8$ heterocycle containing one or two heteroatoms which are N, O or S; unsubstituted $C_3$-$C_{30}$ heteroalkenyl containing one or two heteroatoms which are N, O or S; substituted $C_3$-$C_{30}$ heteroalkenyl containing one or two heteroatoms which are N, O or S; unsubstituted $C_3$-$C_{30}$ heteroalkynyl containing one or two heteroatoms which are N, O and S; substituted $C_3$-$C_{30}$ heteroalkynyl containing one or two heteroatoms which are N, O and S; unsubstituted $C_6$-$C_{18}$ heteroaryl containing one or two heteroatoms which are N, O or S; substituted $C_6$-$C_{18}$ heteroaryl containing one or two heteroatoms which are N, O or S; unsubstituted $C_7$-$C_{30}$ heteroaralkyl containing one or two heteroatoms which are N, O or S; and substituted $C_7$-$C_{30}$ heteroaralkyl containing one or two heteroatoms which are N, O or S; and
(B) $R_3$ is:

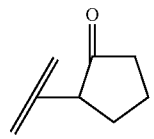

with the proviso that when $R^X$ and $R^Y$ are ethyl, $R^3$ cannot be 3-oxo-cyclopentyl.

13. The compound 3-(dicyclohexylphosphino)cyclohexan-1-one.

14. The compound 3-(di(iso-butyl)phosphino)cycloexan-1-one.

15. A method of making a compound of formula I, as defined in claim 1, the method comprising contacting a compound of formula II:

(II)

wherein:
$R^7$ is hydrogen, $R^1$ or $R^3$, and
$R^8$ is a hydrogen, $R^2$ or $R^3$,
with a cyclic alpha, beta-unsaturated carbonyl compound selected from:

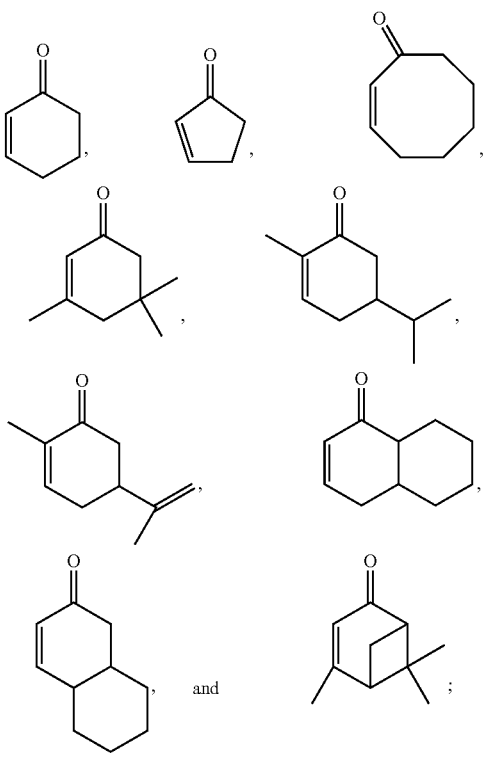

with the proviso that when $R^7$ and $R^8$ are ethyl, the cyclic alpha, beta-unsaturated carbonyl compound cannot be 2-cyclopenten-1-one.

16. The method of claim 15, wherein $R^7$ is $R^1$ or $R^3$ and $R^8$ is $R^2$ or $R^3$.

17. The method of claim 15, wherein:
  (a) $R^7$ is $R^1$ or $R^3$ and $R^8$ is hydrogen; or
  (b) $R^7$ is hydrogen and $R^8$ is $R^2$ or $R^3$.

18. The method of claim 15, wherein $R^7$ and $R^8$ are both hydrogen.

19. The method of claim 15, wherein each of $R^1$ and $R^2$ is independently an unsubstituted $C_1$-$C_{18}$ alkyl, an unsubstituted $C_3$-$C_8$ cycloalkyl, or an unsubstituted $C_6$-$C_{10}$ aryl.

20. The method of claim 19, wherein each of $R^1$ and $R^2$ is independently selected form the group consisting of unsubstituted, branched $C_4$-C18 alkyl, unsubstitute $C_3$-$C_8$ cycloalkyl, and unsubstituted $C_6$-$C_{10}$ aryl.

21. The method of claim 20 wherein each of $R^1$ and $R^2$ is independently selected from the group consisting of: isobutyl, tert-butyl, n-pentyl, iso-pentyl, cyclopenty , cyclohexyl, phenyl, norbomyl, cyclooctyl, and (2,4,4-trimethyl) pentyl.

22. The method of claim 21, wherein $R^1$ and $R^2$ are both iso-butyl.

23. The method of claim 21, wherein $R^1$ and $R^2$ are both cyclohexyl.

24. The method of claim 16, wherein $R^7$ is $R^1$ and $R^8$ is $R^2$, and $R^1$, $R^2$ and the phosphorus atom to which $R^1$ and $R^2$ are bonded form a seven-to ten-membered heterobicycle.

25. The method of claim 24, wherein the heterobicycle is selected from the group consisting of:
  9-phosphabicyclo[3.3.1]nonane,
  9-phosphabicyclo[4.2.1]nonane,
  9-phosphabicyclo[3.3.1]nonanone,
  4,8-dimethyl-2-phosphabicyclo[3.1.1]nonane, and
  2,5-di ($C_1$-$C_4$ alkyl)-7-phosphabicyclo[2.2.1]hept-7-yl.

26. A method of making a compound of formula I, as defined in claim 1, the method comprising contacting a compound of formula II:

wherein:
  $R^7$ is a hydrogen, $R^1$ or $R^3$, and
  $R^8$ is a hydrogen, $R^2$ or $R^3$,
with:

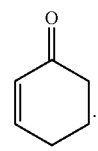

27. A method of making a compound of formula I, as defined in claim 1, the method comprising contacting a compound of formula II:

wherein:
  $R^7$ is a hydrogen, $R^1$ or $R^3$, and
  $R^8$ is a hydrogen, $R^2$ or $R^3$,
with:

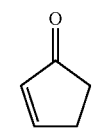

with the proviso that when $R^7$ and $R^8$ are ethyl, the cyclic alpha, beta-unsaturated carbonyl compound cannot be 2-cyclopenten-1-one.

28. The compound 3-(9-phosphabicyclo[3.3.1]nonan-9-yl)-cyclohexan-1-one.

29. The compound di(cyclohexanon-3-yl)-cyclohexylphosphine.

* * * * *

UNITED STATES PATENT AND TRADEMARK OFFICE
CERTIFICATE OF CORRECTION

PATENT NO. : 7,608,713 B2
APPLICATION NO. : 10/548777
DATED : October 27, 2009
INVENTOR(S) : Bradaric-Baus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 262 days.

Signed and Sealed this

Fourteenth Day of December, 2010

David J. Kappos
*Director of the United States Patent and Trademark Office*